(12) United States Patent
Gerwick et al.

(10) Patent No.: US 8,598,313 B2
(45) Date of Patent: Dec. 3, 2013

(54) COMPOSITIONS FOR AMELIORATING CELL PROLIFERATIVE DISORDERS AND METHODS OF MAKING AND USING THEM

(75) Inventors: William H. Gerwick, La Jolla, CA (US); Kevin Tidgewell, Pittsburgh, PA (US); Frederick A. Valeriote, Detroit, MI (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/581,288

(22) PCT Filed: Mar. 11, 2011

(86) PCT No.: PCT/US2011/028029
§ 371 (c)(1),
(2), (4) Date: Nov. 1, 2012

(87) PCT Pub. No.: WO2011/112893
PCT Pub. Date: Sep. 15, 2011

(65) Prior Publication Data
US 2013/0045925 A1 Feb. 21, 2013

Related U.S. Application Data

(60) Provisional application No. 61/313,266, filed on Mar. 12, 2010.

(51) Int. Cl.
*A61K 38/12* (2006.01)
(52) U.S. Cl.
USPC .......................................................... 530/317
(58) Field of Classification Search
None
See application file for complete search history.

(56) References Cited

FOREIGN PATENT DOCUMENTS

WO    WO 2009/032338    *   3/2009

OTHER PUBLICATIONS

Chen, et al. Total synthesis of the marine cyanobacterial cyclodepsipeptide apratoxin A, PNAS, 101(33):12067-12072, 2004.*
Luesch, et al., Total Structure Determination of Apratoxin A, a Potent Novel Cytotoxin from the Marine Cyanobacterium *Lyngbya majuscula*, J. Am. Chem. Soc., 123:5418-5423, 2001.*
Luesch, et al., Ulongamides A-F, New beta-Amino Acid-Containing Cyclodepsipeptides from Palauan Collections of the Marine Cyanobacterium *Lyngbya* sp., J. Nat. Prod., 65:996-1000, 2002.*
Luesch, et al., New Apratoxins of Marine Cyanobacterial Origin from Guam and Palau, Bioorganic & Medicinal Chemistry 10:1973-1978, 2002.*
Tidgewell, Evolved Diversification of a Modular Natural Product Pathway: Apratoxins F and G, Two Cytotoxic Cyclic Depsipeptides from a Palmyra Collection of *Lyngbya bouillonii*, ChemBioChem 2010, 11, 1458-1466.*
Luesch, New Apratoxins of Marine Cyanobacterial Origin from Guam and Palau, Bioorganic & Medicinal Chemistry 10:1973-1978, 2002.*
Gutierrez, Apratoxin D, a Potent Cytotoxic Cyclodepsipeptide from Papua New Guinea Collections of the Marine Cyanobacteria *Lyngbya majuscula* and *Lyngbya sordida*, J. Nat. Prod. 71:1099-1103, 2008.*

* cited by examiner

*Primary Examiner* — Cecilia J Tsang
*Assistant Examiner* — Khalid Kader
(74) *Attorney, Agent, or Firm* — Gregory P. Einhorn; Gavrilovich, Dodd & Lindsey LLP (57) ABSTRACT

In alternative embodiments, the invention provides apratoxin F and apratoxin G compounds, which include apratoxin F and apratoxin G stereoisomers, derivatives and analogs compositions and methods. In alternative embodiments, the invention provides pharmaceutical compositions and formulations comprising apratoxin F (compound 6 of FIG. 1) and apratoxin G (compound 7 of FIG. 1) and their stereoisomers, derivatives and analogs. In alternative embodiments, pharmaceutical compositions and formulations of the invention are administered in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition (e.g., allergy) or infection having a hyperproliferative cell growth component.

18 Claims, 7 Drawing Sheets

Table 1. NMR Spectroscopic Data (600 MHz, CDCl₃) for Apratoxin F (6) and Apratoxin G (7)

| | Apratoxin F (6) | | | Apratoxin G (7) | | |
|---|---|---|---|---|---|---|
| | δC, mult | δH, (J in Hz) | HMBC | δC, mult | δH, (J in Hz) | HMBC |
| NMeAla | | | | | | |
| 1 | 173.6, qC | | | 173.3, qC | | |
| 2 | 54.4, CH | 4.47 d(7.2) | 1, 3, 5 | 54.3, CH | 4.46 q(7.8) | 1, 3, 5, 6 |
| 3 | 14.8, CH₃ | 1.44 d(7.8) | 2 | 15.0, CH₃ | 1.43 d(7.8) | 1, 2 |
| 5 | 31.1, CH₃ | 3.27 s | 1, 2, 6 | 31.2, CH₃ | 3.28 s | 2, 3, 6 |
| NMeIle | | | | NMeVal | | |
| 6 | 173.0, qC | | | 173.7, qC | | |
| 7 | 54.8, CH | 5.48 d(11.4) | 5, 6, 8, 9, 11, | 58.0, CH | 5.26 d(11.4) | 6, 8, 9, 12, 13 |
| 8 | 31.7, CH | 2.26 m | 7, 10, 11 | 27.5, CH | 2.22 m | 7, 9, 10 |
| 9a | 24.6, CH₂ | 0.96 m | 7, 8, 10 | 19.7, CH₃ | 0.95 d(6.6) | 7, 8, 10 |
| 9b | | 1.3 m | 7, 8, 10 | | | |
| 10 | 8.8, CH₃ | 0.89 s | 9 | 18.9, CH₃ | 0.72 d(6.0) | 7, 8, 9 |
| 11 | 13.9, CH₃ | 0.92 d (6.6) | 7, 8 | | | |
| 12 | 30.4, CH₃ | 2.68 s | 7, 13 | 30.3, CH₃ | 2.66 s | 7, 13 |
| NMeAla | | | | NMeAla | | |
| 13 | 170.0, qC | | 15 | 170.4, qC | | |
| 14 | 60.6, CH | 3.28 m | 13, 14 | 60.5, CH | 3.28 m | 13, 14 |
| 15 | 14.1, CH₃ | 1.22 d(6.6) | 13, 14, 17 | 14.1, CH₃ | 1.18 d(6.6) | 13, 14, 17 |
| 16 | 36.7, CH₃ | 2.79 s | | 36.9, CH₃ | 2.80 s | |

FIG. 4

| Position | δC, type | δH (J in Hz) | HMBC | Position | δC, type | δH (J in Hz) | HMBC |
|---|---|---|---|---|---|---|---|
| OMeTyr | | | | OMeTyr | | | |
| 17 | 170.4, qC | | | 17 | 170.6, qC | | |
| 18 | 50.5, CH | 5.05 dd(4.8, 10.2, 10.2) | 17, 19, 27 | 18 | 50.4, CH | 5.04 ddd(4.8, 10.2, 10.2) | 17, 19, 20, 27 |
| 19a | 37.2, CH$_2$ | 2.87 dd(4.8, 12.6) | 17, 18, 20, 21, | 19a | 37.5, CH$_2$ | 2.88 dd(4.8, 12.0) | 17, 18, 20, 21, 25 |
| 19b | | 3.10 d(11.4) | 17, 18, 20, 21, | 19b | | 3.07 dd(12.0, 12.0) | 17, 18, 20, 21, 25 |
| 20 | 128.2, qC | | | 20 | 128.2, qC | | |
| 21/25 | 130.6, CH | 7.16 d(8.4) | 19, 20, 22, 23, | 21/25 | 130.6, CH | 7.14 d(8.4) | 19, 22, 23, 24 |
| 22/24 | 113.9, CH | 6.8 d(9.0) | 20, 21, 23, 25 | 22/24 | 114.0, CH | 6.80 d(9.0) | 20, 23 |
| 23 | 158.6, qC | | | 23 | 158.9, qC | | |
| 26 | 55.3, CH$_3$ | 3.78 s | 23 | 26 | 55.3, CH$_3$ | 3.78 s | 23 |
| NH | | 6.07 d(9.6) | 27 | NH | | 6.13 d(9.0) | 18, 27 |
| MoCys | | | | MoCys | | | |
| 27 | 169.5, qC | | | 27 | 169.6, qC | | |
| 28 | 130.6, qC | | | 28 | 130.2, qC | | |
| 29 | 136.2, CH | 6.37 d(9.0) | 27, 31, 32 | 29 | 136.4, CH | 6.44 d(9.6) | 27, 28, 31, 32 |
| 30 | 72.4, CH | 5.25 ddd(4.2, 9.3, 9.3) | 28, 29, 33 | 30 | 72.4, CH | 5.27 ddd(4.2, 9.6, 9.6) | 28, 29, 33 |
| 31a | 37.6, CH$_2$ | 3.15 dd(4.2, 4.2) | 29, 30, 33 | 31a | 37.7, CH$_2$ | 3.17 dd(3.6, 10.8) | 29, 30, 33 |
| 31b | | 3.46 dd(8.4, 11.1) | 29, 30 | 31b | | 3.47 dd(8.7, 11.1) | 29, 30 |
| 32 | 13.3, CH$_3$ | 1.97 s | 27, 28, 29 | 32 | 13.3, CH$_3$ | 1.98 s | 27, 28, 29 |

*FIG. 4 (Cont'd)*

| Polyketide | | | | Polyketide | | | |
|---|---|---|---|---|---|---|---|
| 33 | 177.3, qC | | | 33 | 177.8, qC | | |
| 34 | 48.8, CH | 2.64 dd(7.2, 10.2) | 33, 35, 44 | 34 | 48.8, CH | 2.63 dd(7.2, 10.2) | 33, 35, 44 |
| 35 | 71.7, CH | 3.56 dddd(3.0, 10.5, 10.6, | | 35 | 71.8, CH | 3.54 dddd(2.4, 10.6, 10.8, | |
| 36a | 38.3, CH$_2$ | 1.11 m | 45 | 36a | 38.5, CH$_2$ | 1.11 m | 45 |
| 36b | | 1.47 m | 34, 35, 37, 45 | 36b | | 1.47 m | 34, 35, 37, 45 |
| 37 | 24.3, CH | 2.14 m | | 37 | 24.4, CH | 2.13 m | |
| 38a | 37.7, CH$_2$ | 1.26 m | 37, 45 | 38a | 37.5, CH$_2$ | 1.25 m | 37 |
| 38b | | 1.79 ddd(2.4, 13.2, 13.2) | 37, 39 | 38b | | 1.78 ddd(3.0, 12.6, 12.6) | 37, 39, 45 |
| 39 | 77.2, CH | 4.88 dd(1.8, 12.6) | 1, 40, 41, 42, | 39 | 77.3, CH | 4.88 dd(2.4, 12.6) | 1, 38, 40, 41, 42, |
| 40 | 34.9, qC | | | 40 | 35.0, qC | | |
| 41 | 26.1, CH$_3$ | 0.88 s | 39, 40, 42, 43 | 41 | 26.2, CH$_3$ | 0.88 s | 39, 40, 42, 43 |
| 42 | 26.1, CH$_3$ | 0.88 s | 39, 40, 41, 43 | 42 | 26.2, CH$_3$ | 0.88 s | 39, 40, 41, 43 |
| 43 | 26.1, CH$_3$ | 0.88 s | 39, 40, 41, 42 | 43 | 26.2, CH$_3$ | 0.88 s | 39, 40, 41, 42 |
| 44 | 16.7, CH$_3$ | 1.06 d(6.6) | 33, 34, 35 | 44 | 16.6, CH$_3$ | 1.06 d(7.2) | 30, 33, 34, 35 |
| 45 | 19.8, CH$_3$ | 1.00 d(6.6) | 36, 37, 38, 39 | 45 | 19.0, CH$_3$ | 0.99 d(6.6) | 36, 37, 38 |
| OH | | 4.52 d(10.8) | 35, 36 | OH | | 4.51 d(10.8) | 35, 36 |

[Table 1 NMR Spectroscopic Data continued - Figure 4 continued]

FIG. 4 (Cont'd)

COMPOSITIONS FOR AMELIORATING CELL PROLIFERATIVE DISORDERS AND METHODS OF MAKING AND USING THEM

CROSS-REFERENCE TO RELATED APPLICATIONS

This United States utility patent application incorporates by reference and is the §371 national phase of PCT international patent application no. PCT/US2011/028029, filed Mar. 11, 2011, which claims benefit of priority to U.S. Provisional Patent Application Ser. No. 61/313,266, filed Mar. 12, 2010. The aforementioned applications are expressly incorporated herein by reference in their entirety and for all purposes.

GOVERNMENT RIGHTS

This invention was made with government support under grant CA100851 awarded by the National Institutes of Health (NIH). The government has certain rights in the invention.

TECHNICAL FIELD

This invention generally relates to drug discovery, medicine and cell biology. In particular, in alternative embodiments, the invention provides apratoxin F and apratoxin G compounds, which include apratoxin F and apratoxin G stereoisomers, derivatives and analogs compositions and methods. In alternative embodiments, the invention provides pharmaceutical compositions and formulations comprising apratoxin F (compound 6 of FIG. 1) and apratoxin G (compound 7 of FIG. 1) and their stereoisomers, derivatives and analogs. In alternative embodiments, pharmaceutical compositions and formulations of the invention are administered in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition or infection having a hyperproliferative cell growth component.

BACKGROUND

Marine cyanobacteria are especially well endowed with these types of modular biosynthetic pathways which they employ to produce a rich arsenal of bioactive secondary metabolites. For example, apratoxin A is a depsipeptides showing subnanomolar cytotoxicity to several different cancer cell lines in vitro. Unfortunately, in evaluating apratoxin A for in vivo anticancer activity, it showed limited or no activity against tumors (colon and breast) at sub-lethal doses, and at higher doses, animal toxicity and weight loss were observed.

Apratoxin B and C are simple desmethyl analogs of apratoxin A isolated from collections of *Lyngbya* sp. Apratoxin D, found in Papua New Guinea, has a carbon skeleton which appears to result from an additional PKS element (as compared to Apratoxins A, B and C) in the biosynthetic pathway. An apratoxin E isolated from a collection of *Lyngbya bouillonii* made in Guam is an analog with several changes to the decorated structure of apratoxin A.

Apratoxin A has been shown to induce a G1-phase cell cycle arrest and apoptosis via interaction with STAT3 and FGFR signaling; and studies determined that the inhibition of STAT phosphorylation is caused by down regulation of an IL-6 transducer and several cancer specific receptor tyrosine kinases. These alterations resulted in prevention of the translocation of several proteins involved in the secretory pathway and is reversible in normal cells but not in cancer cells. One study showed that an oxazoline analog of apratoxin A interacts with Hsp90, a well known and important cancer cell target.

SUMMARY

In alternative embodiments, the invention provides compositions and methods for administration to an individual, e.g., a human, in need thereof in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition or infection having a hyperproliferative cell growth component.

In alternative embodiments, the invention provides compounds or compositions selected from the group consisting of:

apratoxin F (compound 6 of FIG. 1);
apratoxin G (compound 7 of FIG. 1);
a compound having the formula wherein
$R_1$=H, $CH_3$
$R_2$=H, $CH_3$, i-Pr, t-Bu
$R_3$=H, $CH_3$, i-Pr, $CH(CH_3)CH_2CH_3$, $CH_2CH(CH_3)_2$
$R_4$=H, $CH_3$, i-Pr, $CH(CH_3)CH_2CH_3$, $CH_2CH(CH_3)_2$
$R_5$=H, $CH_3$, i-Pr, $CH(CH_3)CH_2CH_3$, $CH_2CH(CH_3)_2$
$R_6$=$CH_2PhOH$, $CH_2PhOMe$, $CH_2Ph$
X=O, S, N;

wherein
$R_1$=H, $CH_3$
$R_2$=H, $CH_3$, i=Pr, t-Bu
$R_3$=H, $CH_3$, i-Pr, $CH(CH_3)CH_2CH_3$, $CH_2CH(CH_3)_2$
$R_4$=H, $CH_3$, i-Pr, $CH(CH_3)CH_2CH_3$, $CH_2CH(CH_3)_2$
$R_5$=$CH_2PhOH$, $CH_2PhOMe$, $CH_2Ph$
X=O, S, N;
any combination thereof; and
stereoisomers, derivatives and analogs thereof;
with the proviso that the compound is not apratoxin A.

In alternative embodiments, one, several or all of the $R_1$, $R_2$, $R_3$, $R_4$, $R_5$ or $R_6$ groups can be any alky, alkene, phenoxy, or alkoxy group. In alternative embodiments, $R_1$, $R_2$, $R_3$, $R_4$, $R_5$ or $R_6$ are independently selected from the group consisting of hydrogen, halo, hydroxy (—OH), phenoxy, thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—NO$_2$), alkoxy, haloalkoxy, thioalkoxy, alkanoyl, haloalkanoyl and carbonyloxy.

As noted above, in alternative embodiments X can be O, S or N.

In alternative embodiments the compositions and compounds of the invention are formulated as a pharmaceutical composition, or formulated for enteral or parenteral administration. For example, in alternative embodiments, formulation or pharmaceutical compositions of the invention comprise: (a) a compound or composition of the invention; a compound selected from the group consisting of: apratoxin F (compound 6 of FIG. 1) and apratoxin G (compound 7 of FIG. 1); and/or stereoisomers, derivatives and/or analogs thereof; or (b) the formulation or pharmaceutical composition of (a), wherein the compound is formulated for administration in vivo; or for enteral or parenteral administration, or as a tablet, pill, geltab, liquid, lotion, aerosol or implant.

In alternative embodiments, the invention provides methods for decreasing or inhibiting cell growth comprising (a) administering to a cell or contacting a cell with a compound of the invention, or a formulation or a pharmaceutical composition of the invention; or (b) the method of (a), wherein the administration is in vitro, ex vivo or in vivo.

In alternative embodiments, the invention provides methods for treating, preventing and/or ameliorating a disease or condition that can be responsive to or ameliorated by decreasing or inhibiting cell growth, e.g., a pathological, uncontrolled or unwanted cell growth, e.g., a cancer or a metastases, or any disease or condition or infection having a hyperproliferative cell growth component, comprising:

(a) administering a compound of the invention, or a formulation or a pharmaceutical composition of the invention, in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition or infection having a hyperproliferative cell growth component;

(b) the method of (a), wherein the administration is to a human or a mammal.

In alternative embodiments, the invention provides methods for ameliorating or preventing an inflammatory disease or condition that can be ameliorated by decreasing or inhibiting cell growth or proliferation, comprising:

(a) administering a compound of the invention, or a formulation or a pharmaceutical composition of the invention, in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition or infection having a hyperproliferative cell growth component;

(b) the method of (a), wherein the administration is to a human or a mammal.

In alternative embodiments, the invention provides kits comprising a compound of the invention, or a formulation or a pharmaceutical composition of the invention.

The compositions and methods of the invention, including the pharmaceutical compositions of the invention, can be useful to treat, reverse, prevent (prophylaxis) or ameliorate any dysfunctional stem cell, or any abnormally (dysfunctional) dividing or metastasizing cancer cells or stem cells, e.g., a cancer stem cell or a tumor stem cell. Cancers that can be treated, prevented or ameliorated by using compositions and methods of this invention include lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and/or any combination thereof.

In alternative embodiments, the invention provides uses of compositions of the invention to treat, reverse, prevent (prophylaxis) or ameliorate any dysfunctional stem cell, or any abnormally (dysfunctional) dividing or metastasizing cancer cells or stem cells, e.g., a cancer stem cell or a tumor stem cell. In alternative embodiments, uses include treating, reversing, preventing or ameliorating cancers, e.g., lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and/or any combination thereof. In alternative embodiments, the invention provides uses of compounds of the invention, or formulations or pharmaceutical compositions of the invention, for treating, preventing and/or ameliorating a disease or condition that can be responsive to or ameliorated by decreasing or inhibiting cell growth, e.g., a pathological, uncontrolled or unwanted cell growth, e.g., a cancer or a metastases, or any disease or condition or infection having a hyperproliferative cell growth component.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 2 graphically illustrates data demonstrating a clonogenic dose response (surviving fraction of cells versus concentration of apratoxin) of: FIG. 2A, apratoxin A (compound 1 of FIG. 1); and, FIG. 2B, apratoxin F (compound 6 of FIG. 1) in HCT-116 cells; as described in detail, below.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

This invention for the first time identifies novel families of apratoxin F and apratoxin G compounds (see FIG. 1), which include apratoxin F and apratoxin G stereoisomers, derivatives and analogs. In alternative embodiments, the invention provides apratoxin F and apratoxin G compounds, including apratoxin F and apratoxin G stereoisomers, derivatives and analogs, and compositions, e.g., pharmaceutical compositions and formulations, comprising apratoxin F and apratoxin G stereoisomers, derivatives and analogs. In alternative embodiments, pharmaceutical compositions and stereoisomers, formulations of the invention are administered in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition or infection having a hyperproliferative cell growth component.

A collection of *Lyngbya bouillonii* from Palmyra Atoll in the Central Pacific, a site several thousand kilometers distant from all previous collections of this chemically prolific species of cyanobacterium, was found to contain two new cancer cell cytotoxins of the apratoxin family—the apratoxin F and apratoxin G of this invention. The structures of these new compounds, apratoxins F and G, were determined by 1-D and 2-D NMR techniques in combination with mass spectrometric methods. Stereochemistry was explored using chromatographic analyses of the hydrolytically released fragments in combination with NMR and optical rotation comparisons with known members of the apratoxin family.

Compositions of the invention, including apratoxins F and G and analogs and stereoisomers, derivatives, add fresh insights into the Structure Activity Relationship (SAR) of apratoxins generally because in alternative embodiments, compositions of the invention incorporate an N-methyl alanine residue at a position where other apratoxins have possessed a proline unit, yet the exemplary apratoxins F and G of the invention retain high potency as cytotoxins to H-460 cancer cells with $IC_{50}$ values of 2 and 14 nM, respectively.

Additional assays using zone inhibition of cancer cells and clonogenic cells give a comparison of the activities of apratoxin F to apratoxin A, as described below. Additionally, these clonogenic studies in combination with maximum tolerated dose (MTD) studies can provide guidelines for in vivo dosing schedules that can be used for formulating and administering compositions of the invention.

While the invention is not based on any particular mechanism of action, these new compositions of the invention (including apratoxins F and G and analogs and stereoisomers, derivatives thereof) can be illustrative of a mechanism, the modification of an non-ribosomal peptide synthetase (NRPS) adenylation domain specificity pocket, for evolving a biosynthetic pathway so as to diversify the suite of expressed secondary metabolites.

While the invention is not based on any particular mechanism of action, several disparate regions of apratoxins F and G and analogs and stereoisomers, derivatives thereof (compositions of the invention) are important for maximal biological activity; however, the connected lower regions from C-39 to the t-butyl terminus and C-1 to C-5 can be more tolerant of structural changes.

Products of Manufacture, Kits

The invention also provides products of manufacture, kits and pharmaceuticals for practicing the methods of this invention. In alternative embodiments, the invention provides products of manufacture, kits and/or pharmaceuticals comprising all the components needed to practice a method of the invention.

Formulations and Pharmaceutical Compositions

In alternative embodiments, the invention provides compositions for use in in vivo, in vitro or ex vivo methods for decreasing or inhibiting cell growth comprising administering to a cell or contacting a cell with a compound or a formulation or a pharmaceutical composition of the invention in vitro, ex vivo or in vivo. In alternative embodiments, the compositions of the invention are used in in vivo, in vitro or ex vivo methods for treating, preventing and/or ameliorating a disease or condition that can be responsive to or ameliorated by decreasing or inhibiting cell growth, e.g., a pathological, uncontrolled or unwanted cell growth, e.g., a cancer or a metastases, or any disease or condition or infection having a hyperproliferative cell growth component. In alternative embodiments, the compositions of the invention are used for ameliorating or preventing an inflammatory disease or condition that can be ameliorated by decreasing or inhibiting cell growth or proliferation.

In alternative embodiments, the pharmaceutical compositions of the invention can be administered parenterally, topically, orally or by local administration, such as by aerosol or transdermally. In alternative embodiments, pharmaceutical compositions can be prepared in various forms, such as granules, tablets, pills, suppositories, capsules, suspensions, salves, lotions and the like. In alternative embodiments, concentrations of therapeutically active compound in a formulation can be from between about 0.1% to about 100% by weight. In alternative embodiments, therapeutic formulations are prepared by any method well known in the art, e.g., as described by Gilman et al., eds., Goodman and Gilman's: The Pharmacological Bases of Therapeutics, 8th ed., Pergamon Press, 1990; Remington: The Science and Practice of Pharmacy, Mack Publishing Co., 20.sup.th ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In alternative embodiments, therapeutic formulation are delivered by any effective means appropriated for a particular treatment. For example, depending on the specific antitumor agent to be administered, the suitable means include oral, rectal, vaginal, nasal, pulmonary administration, or parenteral (including subcutaneous, intramuscular, intravenous and intradermal) infusion into the bloodstream. For parenteral administration, antitumor agents of the present invention may be formulated in a variety of ways. Aqueous solutions of the modulators can be encapsulated in polymeric beads, liposomes, nanoparticles or other injectable depot formulations known to those of skill in the art. In alternative embodiments, compounds of the invention are administered encapsulated in liposomes (see below). In alternative embodiments, depending upon solubility, compositions are present both in an aqueous layer and in a lipidic layer, e.g., a liposomic suspension. In alternative embodiments, a hydrophobic layer comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compositions (e.g., apratoxin F and apratoxin G compounds, and/or apratoxin F and apratoxin G stereoisomers, derivatives and analogs) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. By using liposomes, particularly where the liposome surface carries ligands specific for target cells (e.g., a cancer cell), or are otherwise preferentially directed to a specific tissue or organ type, one can focus the delivery of the active agent into a target cells in an in vivo, in vitro or ex vivo application.

The compositions and formulations of the invention can be directly administered, e.g., under sterile conditions, to an individual (e.g., a patient) to be treated. The modulators can be administered alone or as the active ingredient of a pharmaceutical composition. Compositions and formulations of this invention can be combined with or used in association with other therapeutic agents. For example, an individual may be treated concurrently with conventional chemotherapeutic agents, e.g., those used for tumor and cancer treatment, e.g., daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin or diethylstilbestrol (DES) or any composition known in the art, e.g., as described e.g., in The Merck Manual of Diagnosis and Therapy, 15th Ed., pp. 1206-1228, Berkow et al., eds., Rahay, N.J., 1987.

Nanoparticles, Nanolipoparticles and Liposomes

The invention also provides nanoparticles, nanolipoparticles, vesicles and liposomal membranes comprising compounds used to practice the methods of this invention, e.g., to deliver compositions of the invention (e.g., apratoxin F and apratoxin G compounds, and/or apratoxin F and apratoxin G stereoisomers, derivatives and analogs) to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a cancer cell, a stem cell, a cancer stem cell, a mammalian cell, an epithelial cell, an intestinal epithelial cell, or a mucosal cell and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent (e.g., apratoxin F and apratoxin G compounds, and/or apratoxin F and apratoxin G stereoisomers, derivatives and analogs), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., e.g., apratoxin F and apratoxin G compounds, and/or apratoxin F and apratoxin G stereoisomers, derivatives and analogs) used to practice this invention to a desired cell type (e.g., a cancer cell), as described e.g., in U.S. Pat. Pub. No. 20070110798.

The invention also provides nanoparticles comprising compounds (e.g., e.g., apratoxin F and apratoxin G compounds, and/or apratoxin F and apratoxin G stereoisomers, derivatives and analogs) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention (e.g., apratoxin F, apratoxin G, and analogs and stereoisomers, derivatives thereof) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations of the invention can be administered for prophylactic and/or therapeutic treatments. In therapeutic applications, compositions are administered to a subject already suffering from a cancer, disease, condition, infection or disease in an amount sufficient to cure, alleviate or partially arrest the clinical manifestations of the cancer, disease, condition, infection or disease and/or its complications (a "therapeutically effective amount"). For example, in alternative embodiments, pharmaceutical compositions and formulations of the invention are administered in an amount sufficient to treat, prevent and/or ameliorate a disease or condition that can be ameliorated by decreasing or inhibiting cell growth, e.g., pathological, uncontrolled or unwanted cell growth, e.g., a cancer or a metastases, or any disease or condition (e.g., an allergy) or infection having a hyperproliferative cell growth component.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for oral administration of compositions used to practice the invention are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating a cancer or a metastases, or any disease or condition (e.g., an allergy) or infection having a hyperproliferative cell growth component, and the like. For example, the methods and/or compositions and formulations of the invention can be co-formulated with and/or co-administered with, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

The invention will be further described with reference to the examples described herein; however, it is to be understood that the invention is not limited to such examples.

EXAMPLES

Example 1

Exemplary Compounds of the Invention

This example demonstrates exemplary compounds of the invention, and exemplary methods for making and using them. This example also demonstrates that compositions and formulations of the invention are effective for treating, preventing and/or ameliorating a disease or condition that can be ameliorated by decreasing or inhibiting cell growth, e.g., pathological, uncontrolled or unwanted cell growth, e.g., a cancer or a metastases, or any disease or condition (e.g., allergy) or infection having a hyperproliferative cell growth component.

We collected samples of Lyngbya bouillonii from Palmyra Atoll, a site more than 3200 km from all prior collections of the cyanobacterium. Indeed, upon cancer cell toxicity guided isolation and spectrochemical structure elucidation, this geographically distant sample of Lyngbya bouillonii yielded two novel and highly bioactive natural products in this structure class, the exemplary apratoxins F and G of this invention.
Results and Discussion Palmyra Atoll, approximately 1500 km south-southwest of Honolulu, is an unincorporated territory of the United States that is jointly overseen by the Fish and Wildlife Service, The Nature Conservancy, and a Palmyra Atoll Research Consortium (PARC). Its remote location as one of the northernmost Line Islands contributes to its rich abundance of aquatic wildlife. In 2008, we collected tube-like colonies of the deep red-pigmented cyanobacterium Lyngbya bouillonii (collection code PAL08-16) from reefs 9-15 m deep.[21] Elsewhere in the South and Indo Pacific regions (e.g. Papua New Guinea), L. bouillonii appears more as a sheet-like morphology; however, in both cases the snapping shrimp (Alpheus cf. frontalis) lives in association with the cyanobacterium and is believed responsible for the overt appearance of these colonies.

Microscopically, the cyanobacterial filaments were long (1-3 cm), cylindrical, reddish, and slightly waved. The filaments were 26.3±2.3 µm (n=3) wide and were enclosed with thick and distinct sheaths. Several of the filaments contained hormogonia separated by necridic cells. The vegetative cells were discoid, but relatively long [7.4±1.3 µm long; 24.5±1.8 µm wide; cell width/length ratio=0.3 (n=30)]. The vegetative cells were evenly granulated and their cross-walls were distinctly constricted. The terminal cells were rounded and lacked calyptras or thickened cell walls. The cyanobacterium was collected by hand and preserved in EtOH at low temperature until extraction with $CH_2Cl_2$/MeOH. The extract was subjected to H-460 (non-small lung cancer cells) cancer cell bioassay guided isolation using first NP Vacuum Liquid Chromatography followed by two rounds of RP-HPLC, and yielded 6 and 7 as the active constituents.

Figure 3:
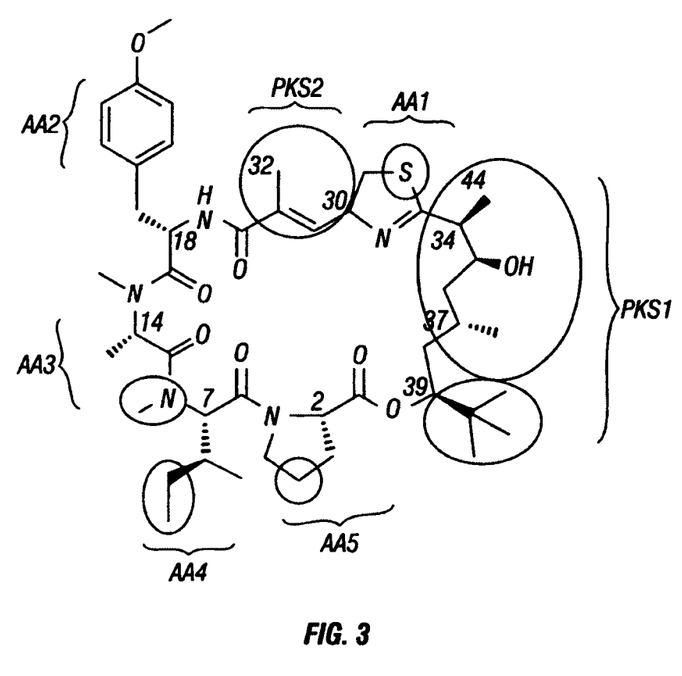
FIG. 3 schematically illustrates that all resonances for the two polyketide chain sections of apratoxin A, including the signature t-butyl group, were present with minimal chemical shift differences in the spectrum of apratoxin F, or compound 6; as described in detail, below.

By a combination of LC-ESI-MS (obs. [M+H]+ m/z 828.30) and HR-ESIMS (obs. [M+Na]+ m/z 850.4800), the molecular formula of the exemplary apratoxin F (6) was determined as $C_{44}H_{69}N_5O_8S$, hence differing from apratoxin A (1) by a single carbon atom and therefore of one less degree of unsaturation. A series of diagnostic NMR signals were highly similar to those reported for apratoxin A (1).[4] Notably, all resonances for the two polyketide chain sections of apratoxin A, including the signature t-butyl group, were present with minimal chemical shift differences in the spectrum of apratoxin F, or compound 6, as illustrated in FIG. 3.

The spin systems and associated 1H and 13C NMR resonances for four of the five amino acids of apratoxin A, namely Cys(thiazoline), O-methyl tyrosine, N-methyl alanine, and N-methyl isoleucine, were also nearly identical to those in the exemplary apratoxin F. Hence, our structure elucidation efforts focused on identification of the final amino acid residue in all cases heretofore, present as an l-proline residue.

Unlike 1, compound 6 possessed a deshielded alpha proton at δ4.47 which was a quartet (J=7.5 Hz) and coupled exclusively to a doublet methyl group at δ1.44. HMBC from the alpha proton at δ4.47 also identified an associated carbonyl at δ173.6. A distinctive N-methyl group was located at δ3.27 and also showed HMBC correlations to the α-carbon (δ54.4) of this residue, thus defining a second N-methyl alanine residue in the exemplary apratoxin F. Finally, the position of this new residue as a replacement for the proline in apratoxin A was shown by HMBC between the α-hydroxy proton at C-39 (δ4.88) and the carbonyl of this second N-Me Ala residue. Similarly, inter-residue HMBC correlations between α-protons and amide carbonyls were used to show an identical linkage between the other residues in 6 to those in 1, and thus completed the planar structure of this new member of the apratoxin family (Table 1, see FIG. 4).

By a combination of LC-ESI-MS (obs. [M+H]+ m/z 814.30) and HR-ESIMS (obs. [M+H]+ m/z 814.4782), the molecular formula of the exemplary apratoxin G (7) was determined as $C_{43}H_{67}N_5O_8S$, hence differing from the exemplary apratoxin F (6) by a single methylene unit. In a similar manner to 6, the spin systems and associated 1H and 13C NMR resonances for four of the five amino acids of 6, namely Cys(thiazoline), O-methyl tyrosine, and two N-methyl alanines were also nearly identical in 7. The final residue was shown to be N-Me-Val by the presence of doublet methyl signals at δ0.72 and δ0.95 and the loss of the doublet signal at δ0.92 along with the multiplet signals at δ0.96, and δ1.3. This change from N-Me-Ile to N-Me-Val accounts for the reduction by a CH2 in the molecular formula determined by HR-MS. Linkage of the amino acid residues was confirmed to be identical to previous apratoxins based on HMBC correlations.

Configurations of compounds 6 and 7 were determined using a combination of techniques, including 1H and 13C NMR chemical shift comparisons with the known apratoxins, acid hydrolysis followed by Marfey's analysis, and overall optical rotation. First, the relative configuration of the comparable chiral centers around the macrocyclic ring could be assigned as the same as in apratoxin A based of the similarity of 1H and 13C NMR chemical shifts and coupling constants (see Supporting Information). Acid hydrolysis of both the exemplary apratoxins F (6) and G (7) followed by Marfey's analysis confirmed the presence and stereochemistry of the three amino acids present in both compounds. Fragments from 6 showed retention times of 22.54, 32.51, 34.60 with masses corresponding to N-Me-Ala, O-Me-Tyr and N-Me-Ile, respectively.

By contrast, fragments from 7 showed retention times of 22.57, 31.36, and 32.53 with masses corresponding to N-Me-Ala, N-Me-Val and O-Me-Tyr, respectively. Pure samples of the constituent amino acids were derivatized and analyzed in the same manner with retention times of: d-O-Me-Tyr (28.00 min), l-O-Me-Tyr (32.57 min), d-N-Me-Ala (21.85 min), l-N-

Me-Ala (22.15 min), d-N-Me-Ile (30.05 min), d-allo-N-Me-Ile (30.40 min), l-N-Me-Ile (34.59 min), l-allo-N-Me-Ile (34.95 min), d-N-Me-Val (27.34 min), l-N-Me-Val (31.31 min). By this analysis, 6 was shown to contain l-N-Me-Ala, 1-O-Me-Tyr, and l-N-Me-Ile while 7 was shown to contain l-N-Me-Ala, 1-O-Me-Tyr, and l-N-Me-Val. Finally, because the optical rotations of 6 and 7 are both large and negative (6, [α]D-249; 7, [α]D-206) and the optical rotation of apratoxin A (1) is of similar sign and magnitude ([α]D-161), they are likely all of the same enantiomeric series.

Figure 1:
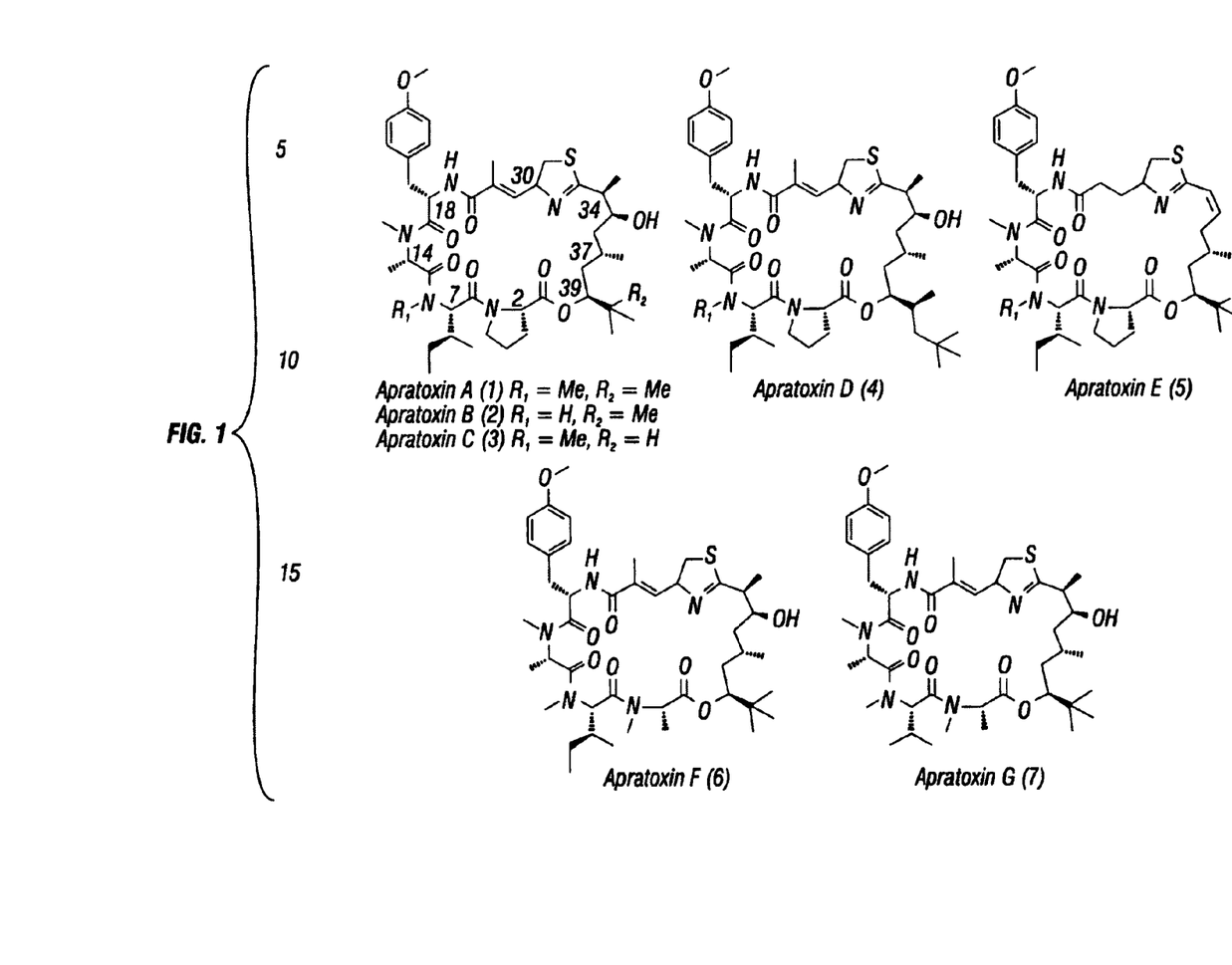
FIG. 1 illustrates apratoxins A (compound 1 of FIG. 1), B (compound 2 of FIG. 1), C (compound 3 of FIG. 1), D (compound 4 of FIG. 1) and E (compound 5 of FIG. 1), and the exemplary compositions of this invention, termed "apratoxin F" and "apratoxin G" (apratoxin F is compound 6 of FIG. 1, and apratoxin G is compound 7 of FIG. 1); as described in detail, below.
Figure 2A:
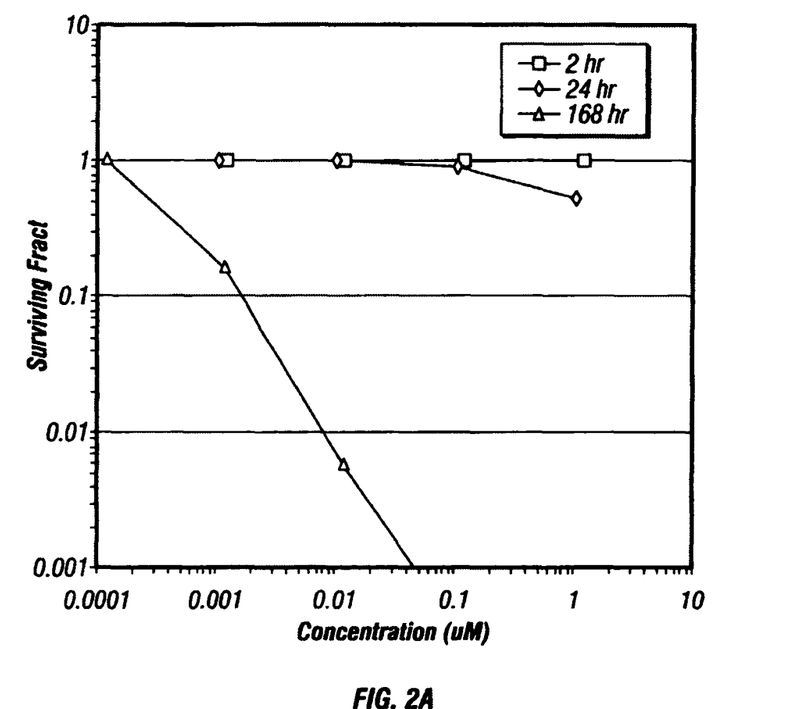
Figure 2B:
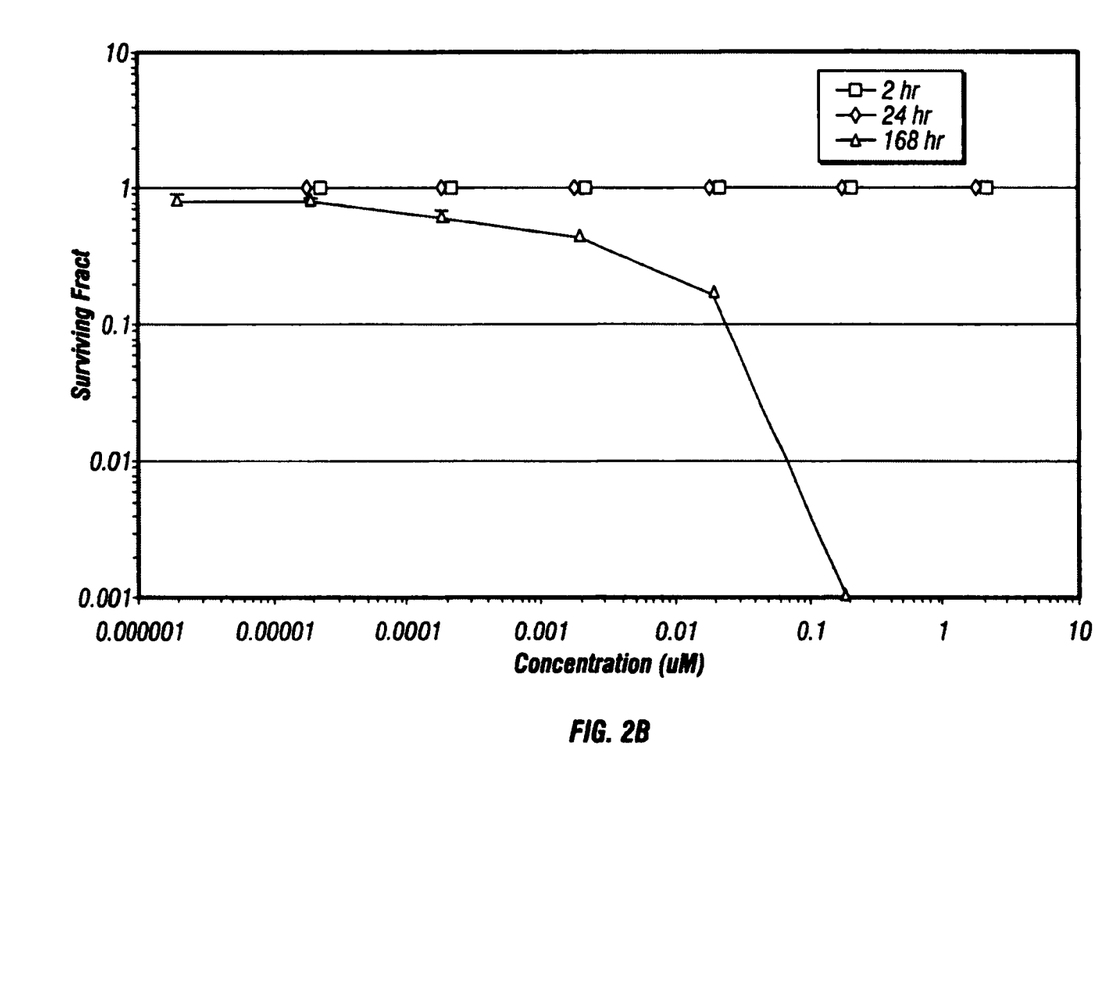

FIG. 2 illustrates a clonogenic dose response of: FIG. 2A, apratoxin A (compound 1 of FIG. 1); and, FIG. 2B, apratoxin F (compound 6 of FIG. 1) in HCT-116 cells. As a result of this bioassay guided isolation process, the exemplary apratoxins F and G of this invention were identified and demonstrated to be major cancer cell and brine shrimp toxins of this Palmyra collection of *L. bouillonii*. In the brine shrimp toxicity assay [22] extract fraction H, containing 6 and 7, showed 98% toxicity at 1 ppm. In the H-460 cancer cell assay, [23] the IC50 value for apratoxin F was 2 nM and for apratoxin G was 14 nM, respectively. For HCT-116 cells, the IC50 values for apratoxin A was 1 ng/ml (1.21 nM) and for apratoxin F was 31 ng/ml (36.7 nM). There was insufficient apratoxin G to test against HCT-116, however, it was less potent that apratoxin F as a mixture of apratoxin F and G yielded an IC50 value of 120 ng/mL against HCT-116 cells.

Zone inhibition disc assays were conducted with 1 and 6 as previously described [24] against an array of cancer cell lines and a normal cell line (Table 2). For comparable zones, the exemplary apratoxin F of the invention was about 10-fold less potent than for apratoxin A, however, both demonstrated solid tumor selectivity against both human tumor cell lines, HCT-116 and H125. Selectivity is noted by a zone differential ≥250 units between the solid tumor and leukemia (CEM) cells.

TABLE 2

| | µg/disk | L1210 | Colon38 | CFU-GM | HCT-116 | H125 | CEM |
|---|---|---|---|---|---|---|---|
| | | Zone Inhibition Assay | | | | | |
| 1 | 3.75 | 650 | 800 | 650 | 650 | 700 | 400 |
| 6 | 8.25 | 700 | 600 | 700 | 800 | 800 | 450 |

A clonogenic concentration-survival study was conducted for 1 and 6 to both define the effect of exposure duration on cytotoxicity and to provide a guide for determining the most effective dose schedule for therapeutic assessment.[24] The clonogenic survival of HCT-116 cells was determined at three different exposure durations: 2 h, 24 h, and continuous (168 h or 7 day), as a function of drug concentration, as illustrated in FIG. 3. The concentration for an exposure duration (t) that yields a surviving fraction of 10% ($_tS_{10}$) was determined: $_2S_{10}$ and $_{24}S_{10}$ for both apratoxin A (see FIG. 3A) and apratoxin F (see FIG. 3B)>>1.2 µM. For $_{168}S_{10}$ the values were 1.6 and 30 nM, respectively. These results indicate that in order to observe a therapeutic effect with HCT-116 cells in vivo, the concentration of these apratoxins would have to be maintained chronically above either 1.6 or 30 nM, respectively.

A preliminary study of the maximum tolerated dose for apratoxin A was found to be 0.6 mg/kg which corresponds to approximately 12 µg/mouse. These data suggest that previous toxicities observed in vivo[4] may be associated with elevated peak plasma levels of 1 from bolus injection and therapeutic efficacy could be achieved with constant dosing to maintain lower plasma levels of drug. Studies on the pharmacokinetics and in vivo anti-tumor activity are ongoing.

Current understanding of the (SAR) in the apratoxin family results from data obtained for both the natural products as well as synthetic and semi-synthetic analogs, see FIG. 3. Briefly, compared to apratoxin A (compound 1 of FIG. 1), apratoxin B (compound 2 of FIG. 1) lacks the isoleucine N-methyl group (30 to 40-fold loss), apratoxin C (compound 3 of FIG. 1) possesses an isopropyl starter unit (2-fold loss), (E)-34,35-dehydro-apratoxin A is a semi-synthetic derivative of apratoxin A, (72-230 fold loss), apratoxin D (compound 4 of FIG. 1) has an extended t-butyl starter unit (roughly equivalent activity), and apratoxin E (compound 5 of FIG. 1) has three modifications including a (Z)-34,35-dehydration, loss of the C-28 methyl group and saturation of the C-28/29 bond (only a modest loss of activity).

From synthetic approaches, it was discovered that replacement of the sulfur in the thiazole ring with an oxygen to create an oxazole was tolerated,[7] a modification which may facilitate the production of a library of apratoxin analogs by solid phase total synthesis.[15] The C-37 methyl group in the polyketide section has been shown to be required, and that its stereochemistry is important to the biological activity.[11] While the C-34 methyl group has also been examined by synthetic approaches, the biological effect of alterations in its configuration has not yet been reported.[12] FIG. 3 illustrates the SAR of the Apratoxin Core for Cytotoxicity. (Red—Alteration not tolerated, Yellow—Alteration has minor affect on activity, Green—Modification allowed.)

The exemplary apratoxin F (compound 6 of FIG. 1) and apratoxin G (compound 7 of FIG. 1) of this invention are the first apratoxin analogs to probe the biological consequence of modifications in the peptidic portion of the apratoxin skeleton, specifically, the biosynthetically-terminating proline residue. Somewhat remarkably, despite all natural and synthetic analogs reported to date possessing a proline residue at this position, these new apratoxins of this invention reveal that this is not a required feature of the molecule. A consequence of this replacement in apratoxin F (compound 6 of FIG. 1) and apratoxin G (compound 7 of FIG. 1) is a loss of rigidity in the lower section of the molecule, thus allowing for some conformational flexibility in these new analogs.

Additionally, apratoxin G (compound 7 of FIG. 1) shows that exchange of the N-methyl isoleucine with an N-methyl valine causes a 7-fold reduction in activity compared to apratoxin F (compound 6 of FIG. 1). Overall, a picture began to emerge wherein features of the Western and Northern portions of the molecule are quite critical for activity, while the Southern section seems quite tolerant of change. Except for modifications to the isoleucine residue, the Eastern quadrant is little explored for its SAR features to date.

The biosynthesis of the apratoxins is predicted to be initiated by a polyketide synthase (PKS1) section which transitions into the NRPS-encoded amino acid portion (AA1 to AA5), interrupted by one short PKS module (PKS2), and terminates with a cyclization to form the final product.[19] Previously reported apratoxin analogues appear to result from altered methylation patterns (Apr B and C), alterations in the number of PKS modules (Apr D), or modifications to the PKS optional domains (Apr E). (FIG. 1).

By contrast, the variations in amino acid composition that are represented by the exemplary apratoxins F and G of this invention result from either alterations in the adenylation domains present in the NRPS genes, or promiscuity in the selected substrate by two of these adenylation domains. For example, the geometrical constraints present in the adenylation specificity pockets encoding for Ile and Val are relatively similar,[25] and lack of substrate discrimination may explain this substitution in the penultimate residue of apratoxin F and G (AA 4).

On the other hand, a substantial change in the amino acid residues at several positions is required to explain the conversion of a proline encoding A-domain specificity pocket into that specifying for an alanine residue.[26] Thus, it appears that this terminal portion of the apratoxin pathway has been modified to the greatest degree when comparing these two geographically divergent populations of *L. bouillonii*. Sequencing of this section of the biosynthetic clusters encoding for apratoxin A and F would be informative as to whether this modification has arisen through mutations to this section of the cluster, or through A-domain swapping via horizontal gene transfer and recombination events. Ultimately, comparison of these clusters will give keen insight into the evolution and diversification of this family of metabolites.

In this regard, to gain some initial insight into the phylogenetic relationships of these different apratoxin-producing strains of *L. bouillonii*, a tree based on the SSU (16S) rRNA gene revealed a shared evolutionary history with other marine Lyngbya species (FIG. 4) and, thus, supported the morphology-based taxonomic characterization above. However, two different copies of the 16S rRNA gene were obtained from the apratoxin F and G producer, with 0.3% sequence divergence between the two copies. Secondary structure modelling pinpointed the nucleotide substitutions between these two copies as compensatory base changes (CBC) positioned at lagging helix strands of the RNA molecules. Based on the conserved nature of the RNA molecule the gene variations were assumed to correspond to different ribosomal operons in the Lyngbya genome.

Figure 4:
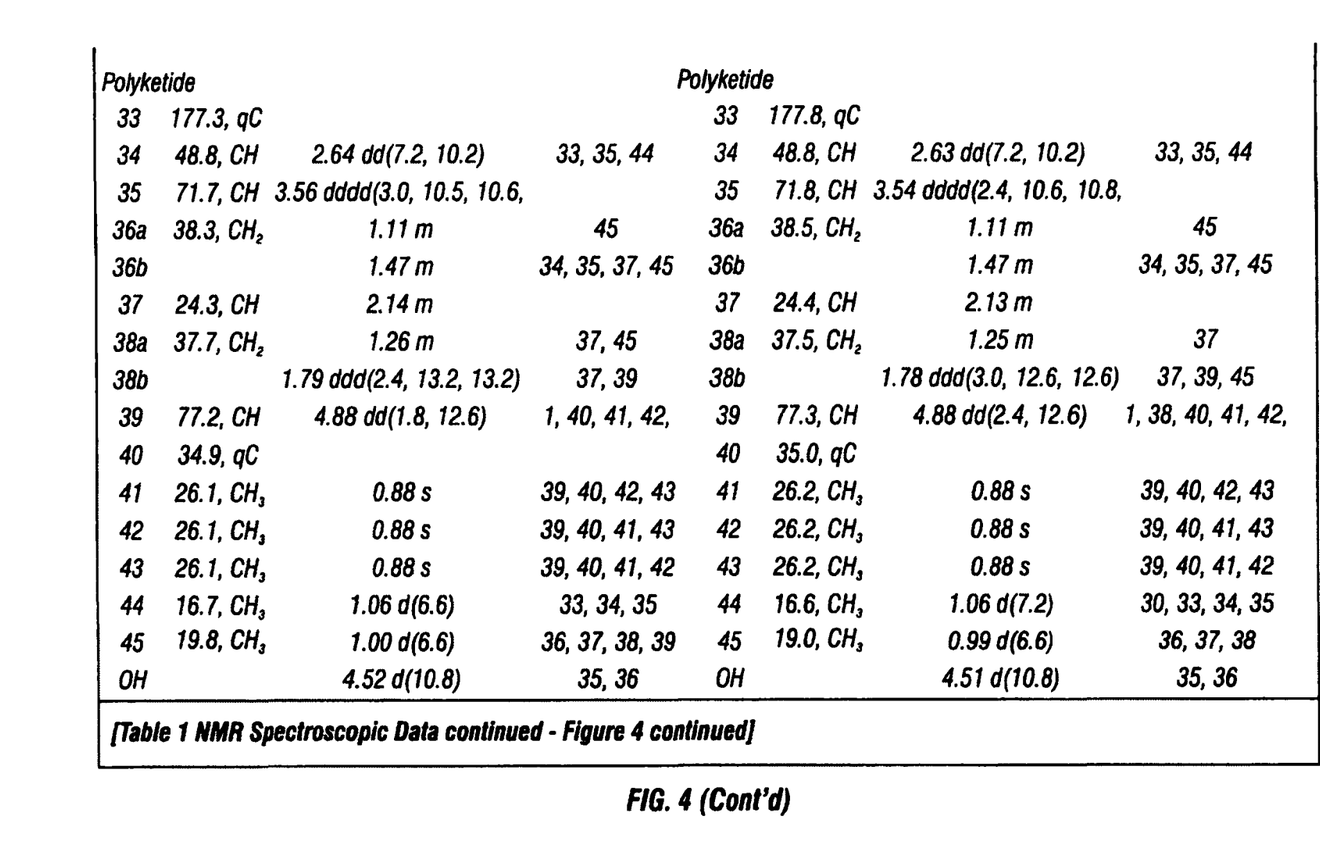
FIG. 4 illustrates Table 1, which sets forth NMR spectroscopic data for apratoxin A and apratoxin F, including NMR chemical shift comparisons; as described in detail, below.

FIG. 4 illustrates a maximum-likelihood (PhyML) phylogenetic tree of the apratoxin F-G producer *Lyngbya bouillonii* PAL08-16 with other apratoxin-producing strains and marine *Lyngbya* species based on 16S sequence. *Escherichia coli* J01695 and *Gloeobacter violaceus* PCC 7421 were used as outgroups and type strains of the cyanobacterial lineages: *Trichodesmium, Oscillatoria, Microcoleus, Planktothrix, Symploca, Geitlerinema, Limnothrix* and *Leptolyngbya* were added to enhance the evolutionary perspective. The support values at important nodes are indicated as boot-strap (ML), posterior probability (MrBayes) and boot-strap (MP). Specimens are designated as taxa, strain and acc. Nr. in brackets.

To gain further insight into the phylogenetic differences between this new chemotype and other apratoxin-producing *L. bouillonii* strains, a multi locus sequencing typing (MLST) comparison was performed with an apratoxin A-C producer from Papua New Guinea. Three common house-keeping genes composed of: (i) the 16S rRNA gene, (ii) the 16S-23S internal transcribed spacer (ITS) intergenic region, (iii) and the RNA polymerase γ-subunit (rpoC1) encoded gene were analyzed. Phylogenetic- and BLAST-analysis of each housekeeping gene supported the overall phylogenetic relatedness obtained from the 16S rRNA gene. (FIG. 4) In accordance with the ribosomal genes, the 16S-23S ITS-regions were also obtained in two variable copies per genome. The four ITS-regions shared an average gene sequence identity of 89.7% within the genomes and 90.5% between the two apratoxin chemotypes. The rpoC1 gene was only found as a single-copy gene when sequencing four clones per gene library. The rpoC1 gene varied with 3.2% between the two *L. bouillonii* chemotypes. Unfortunately, there are an insufficient number of rpoC1 gene sequences in public data bases to fully explore the evolutionary histories and relationships between these different apratoxin-producers, but this gene robustly distinguishes these two strains from one another.

CONCLUSION

The exemplary apratoxins F and G of the invention represent two new genuses of the apratoxin family for a variety of reasons. The exemplary apratoxins F and G are the first which posses significant alterations of the amino acid composition in the peptidic portion of the apratoxin skeleton. Secondly, the exemplary apratoxins F and G retain potent cancer cell cytotoxicity despite these alterations in constituent amino acids, thus revealing a previously unrecognized site of potential structural tolerance in the apratoxin family of cancer cell toxins. Thirdly, the producing organism was collected from a location very distant from previous collections of *L. bouillonii*, and there was no evidence of any of the other known apratoxin analogs present in its extracts. Thus, it appears that the apratoxin biosynthetic gene cluster has evolved between these two geographically distinct populations of *Lyngbya bouillonii*, presumably in response to differing environmental pressures, so as to diversify the suite of its cytotoxic natural products.

EXPERIMENTAL SECTION

General Experimental Procedures. Optical rotations were measured with a JASCO P-2000™ polarimeter. UV spectra were measured on a Beckman Coulter DU800™ spectrophotometer while IR spectra were recorded on a Nicolet IR 100 FT-IR spectrophotometer. NMR spectra were acquired on a Varian NOVA 600™ MHz spectrometer and referenced to residual solvent $^1$H and $^{13}$C signals ($\delta$H 7.26, $\delta$C 77.0 for $CDCl_3$). Low-resolution ESI-MS were acquired on a Finnigan LCQ ADVANTAGE MAX™ mass spectrometer, while high-accuracy mass measurements were obtained on an Agilent ESI-TOF mass spectrometer. Purification of the compounds was carried out on a Waters HPLC system equipped with a Waters 515 binary pump and a Waters 996™ PDA detector.

Biological Material Collection and Identification. The marine cyanobacterium *Lyngbya bouillonii* PAL08-16 was collected from a depth of 9-15 m from Palmyra Atoll (N 05°52.021, W 162°03.262) using SCUBA. The samples were stored in 1:1 EtOH/$H_2O$ and frozen at −20° C. Specimens for genetic analysis (approximately 200 mg) were preserved in 10 mL RNALATER™ (RNAlater®) (Ambion Inc., Austin, Tex., USA). A voucher specimen is available from WHG as collection number PAL 08-16-08-3.

Morphological Characterization. Morphological characterizations were performed using an Olympus IX51™ epifluorescent microscope (100×) equipped with an Olympus U-CMAD3™ camera. Measurements were provided as: mean±standard deviation (SD). The filament means were the average of three filament measurements and cell measurements the average of ten adjacent cells of three filaments. Taxonomic identification of cyanobacterial specimens was performed in accordance with modern taxonomic systems.[28, 29]

DNA Extraction, PCR and Cloning. Genomic DNA was extracted from ~40 mg of cleaned cyanobacterial filaments using the WIZARD® Genomic DNA Purification Kit (Promega) following the manufacturer's specifications. The isolated DNA was further purified using a GENOMIC-TIP 20/G™ kit (Qiagen). DNA concentration and purity was measured on a DU® 800™ spectrophotometer (Beckman Coulter) at a 1:10 dilution. The 16S rRNA genes were PCR-amplified using the cyanobacterial-specific primers 106F and 1509R,[30] the rpoC1 genes using the degenerate primers LrpoC1-F and LrpoC1-R,[27] and the 16S-23 ITS region using 320-340 primers.[31] The PCR reaction volumes were 25 µL containing 0.5 µL (approximately 50 ng) of DNA, 2.5 µL of 10×PFUULTRAT™ (PfuUltra IV™) reaction buffer, 0.5 µL (25 mM) of dNTP mix, 0.5 µL of each primer (10 µM), 0.5 µL of PFUULTRAT™ fusion HS DNA polymerase and 20.5 µL dH$_2$O. The PCR reactions were performed in an EPPENDORF® MASTERCYCLER® gradient as follows: initial denaturation for 2 min at 95° C., 25 cycles of amplification: 20 sec at 95° C., 20 sec at 50° C. and 1.5 min at 72° C., and final elongation for 3 min at 72° C. PCR-products were analyzed on a (1%) agarose-gel in SB-buffer and visualized by EtBr-staining PCR products were subcloned using the ZERO BLUNT® TOPO® PCR Cloning Kit (Invitrogen) into the pCR®-BLUNT IV TOPO® vector, and then transformed into TOPO® cells and cultured on LB-kanamycin plates. Plasmid DNA was isolated using the QIAPREP® (QIAprep®) spin miniprep kit (Qiagen) and sequenced with M13F/M13R primers. Sequencing of the 16S rRNA genes' middle regions were improved using the internal primers 359F and 781R.[30] The gene sequences are available in the DDBJ/EMBL/GenBank databases under the following acc. No.: 16S rRNA gene (rrn A: GU111927; rrn B: GU182894), rpoC1 (GU111928), and 16S-23 ITS (rrn A: GU111929; rrn B: GU111926).

Phylogenetic Inference. All gene sequences were aligned using ClustalW XXL in MEGA 4.0 with standard gap opening and extension penalties without gaps.[32] The secondary RNA structures were predicted by CLC Combined Workbench 3.5.2 (CLC bio, Cambridge, Mass., USA). Mutation types and domains of the 16S rRNA genes were determined by superimposing their secondary structures on the SSU model for *Escherichia coli* J01695.[33] The evolutionary histories of the cyanobacterial genes were inferred using Maximum likelihood (ML), Maximum Parsimony (MP) and Bayesian inference algorithms. Appropriate nucleotide substitution models were selected using Akaike information criterion (AIC) and Bayesian information criterion (BIC) in Modeltest 3.7.[34] The Maximum likelihood (ML) inference was performed using PhyML v2.4.4.[35] The analysis was run using the GTR+I+G model (selected by AIC and BIC criteria) assuming a heterogeneous substitution rates and gamma substitution of variable sites (proportion of invariable sites (pINV)=0.419, shape parameter (a)=0.414, number of rate categories=4). Bootstrap resampling was performed on 500 replicates. Bayesian analysis was conducted using MRBAYES 3.1™ (MrBayes 3.1).[36] The Bayesian inference was performed using the GTR+I+G substitution model (pINV=0.450, α=0.449, number of rate categories=4) with Markov chains (one cold and three heated) ran for 3,000,000 generations. The first 25% were discarded as burn-in and the following data set were being sampled with a frequency of every 100 generations. The MP inference was run using the Maximum Composite Likelihood method. The MP tree was searched using the Close-Neighbor-Interchange (CNI) algorithm at a search level of 1.[37] All positions containing gaps and missing data were eliminated from the dataset (Complete deletion option) for a total of 1372 bp (approximately 95% of the gene coverage).

Extraction and Isolation: *L. bouillonii* 142.9 g (dry wt) was extracted five times with 2:1 CH$_2$Cl$_2$/MeOH and concentrated to dryness in vacuo to give 4.3 g of crude extract. A portion of the crude extract (2.6 g) was subjected to VLC chromatography using a gradient of 0-100% EtOAc in hexanes followed by 0-100% gradient of MeOH in EtOAc to yield nine fractions (A-I). Fraction G [eluted with 100% EtOAc (21.7 mg)], Fraction H [eluted with 50% MeOH in EtOAc (170.4 mg)], and Fraction I [eluted with 100% MeOH (377.7 mg)] showed potent toxicity against brine shrimp and H-460 lung cancer cells. A portion of fraction H (31.5 mg) was further purified by sequential isocratic RP HPLCs [100% MeOH (SYNERGI 10u FUSION RP™ 250×10; 2 mL/min) followed by 85:15 CH$_3$CN/H$_2$O (SYNERGI FUSIO™ 4µ; 2 mL/min)] to give 6.6 mg of apratoxin F and 0.4 mg of apratoxin G as amorphous powders.

Apratoxin F (6): amorphous powder $[\alpha]_D$=−250 (c 0.33, CH$_3$CN); UV (MeOH) $\lambda_{max}$ (log ε) 204 (6.52), 226 (6.33), 282 (5.27) nm; IR (film) v-max 3423 (br), 2963, 1740, 1621, 1511, 1460, 1387, 1247, 1182, 1088 cm-1; $^1$H and $^{13}$C NMR, see Table 1, FIG. 4; ESIMS obs. m/z 828.32, 872.92; HR-ESIMS m/z 850.4800 (calcd for C$_{44}$H$_{69}$N$_5$O$_8$SNa, 850.4765).

Apratoxin G (7): amorphous powder $[\alpha]_D$=−206 (c 0.02, ACN); UV (MeOH) $\lambda_{max}$ (log ε) 204 (6.30), 226 (6.06), 282 (5.07) nm; IR (film) v-max 3423 (br), 2963, 1740, 1621, 1511, 1460, 1387, 1247, 1182, 1088 cm-1; $^1$H and $^{13}$C NMR, see Table 1, FIG. 4; ESIMS m/z 814.30, 859.91; HR-ESIMS m/z 814.4782 (calcd for C$_{43}$H$_{68}$N$_5$O$_8$S, 814.4783).

Hydrolysis and Marfey's Analysis. Samples of 6 (0.5 mg, 0.0006 mmol) and 7 (0.5 mg, 0.0006 mmol) were separately treated with 6 N HCl in sealed vials at 120° C. for 24 h. The solutions were concentrated to dryness under a stream of N$_2$. The dried hydrolysates were then treated with a solution of FDAA (0.25 mg, 0.0009 mmol) in acetone (50 µL) and 0.1 M NaHCO$_3$ (100 µL) and heated to 90° C. for 5 min in sealed vials. The reaction was neutralized with 2 N HCl (50 µL) and diluted with CH$_3$CN (100 µL). The resulting solutions were then analyzed by RP-HPLC-MS using a LICHROSPER™ (LiChrosphere™) C18 column (125×4 mm) and a gradient of 15% CH$_3$CN: 85% acidified H$_2$O (0.1% HCOOH) to 40% CH$_3$CN:60% acidified H$_2$O (0.1% HCOOH) over 45 min at 0.8 mL/min, and monitored using a PDA detector as well as mass. Amino acid standards for chromatographic comparison were treated in identical fashion.

Biological Activity. Brine shrimp (*Artemia salina*) toxicity was measured as previously described.[22] After a 24 h hatching period, aliquots of 10 mg/mL stock solutions of sample were added to test wells containing 5 mL of artificial seawater and brine shrimp to achieve a final range of concentrations from 1 to 100 ppm. After 24 h the live and dead shrimp were tallied.

Cytotoxicity was measured in NCI H-460 human lung tumor cells with cell viability being determined by MTT reduction.[23] Cells were seeded in 96-well plates at 6000 cells/well in 180 µL of medium. After 24 h, the test chemicals were dissolved in DMSO and diluted into medium without fetal bovine serum and then added at 20 µg/well. DMSO was less than 0.5% of the final concentration. After 48 h, the medium was removed and cell viability determined.

Cytotoxicity was measured in HCT-116 cells using a hemocytometer. These cells were grown in 5 mL culture medium (RPMI-1640+15% FBS containing 1% penicillin-streptomycin and 1% glutamine) at 37° C. and 5% CO$_2$ at a starting concentration of 5×10$^4$ cells/T25 flask. On day 3, cells were exposed to different concentrations of the drug. Flasks were incubated for 120 h (5 days) in a 5% CO$_2$ incubator at 37° C., and the cells were harvested with trypsin, washed once with HBSS, and then resuspended in HBSS and counted using a hemocytometer. The results were normalized to an untreated control and $IC_{50}$ values determined using Excel.

Clonogenic concentration- and time-survival studies were carried out with HCT-116. These cells were grown in 5 mL culture medium (RPMI-1640+15% FBS containing 1% penicillin-streptomycin and 1% glutamine) at 37° C. and 5% $CO_2$ at a starting cell density of $5\times10^4$ cells/T25 flask. On day 3, cells were exposed to different concentrations of the drug. Apratoxin A (compound 1 in FIG. 1) or the exemplary Apratoxin F of the invention (compound 6 in FIG. 1) was added to the medium (RPMI+10% FBS) to a final concentration of 1 μg/mL (1.2 μM) and 10-fold dilutions thereof. At either 2 or 24 h, the cells were removed, washed and seeded at 200 or 20,000 cells in 60 mm dishes. For continuous exposure to drug, the medium containing the compounds remained in contact with the cells for the entire incubation period (168 h). The dishes were incubated for 7 days, the medium was removed, and the colonies were stained with methylene blue. Colonies containing 50 cells or more were counted. The results were normalized to an untreated control. Plating efficiency for the untreated cells was about 90%.

REFERENCES

[1] P. M. Dewick, Medicinal Natural Products: A Biosynthetic Approach, Wiley, West Sussex, UK, 2009, p. 539.
[2] L. T. Tan, Phytochemistry. 2007, 68, 954-79.
[3] K. Tidgewell, et al., The Natural Products Chemistry of Cyanobacteria in Comprehensive Natural Products Chemistry, $2^{nd}$ Ed., (Eds.: B. Moore, P Crews), Elsevier, Oxford, 2010.
[4] H. Luesch, et al., J Am Chem Soc 2001, 123, 5418-23.
[5] H. Luesch, et al., Bioorg Med Chem 2002, 10, 1973-8.
[6] M. Gutierrez, T. L. Suyama, N. Engene, J. S. Wingerd, T. Matainaho, W. H. Gerwick, J Nat Prod 2008, 71, 1099-103.
[7] S. Matthew, P. J. Schupp, H. Luesch, J Nat Prod 2008, 71, 1113-6.
[8] J. Chen, C. J. Forsyth, J Am Chem Soc 2003, 125, 8734-5.
[9] J. Chen, C. J. Forsyth, Proc Natl Acad Sci USA 2004, 101, 12067-72.
[10] T. Doi, Y. Numajiri, A. Munakata, T. Takahashi, Org Lett 2006, 8, 531-4.
[11] D. Ma, B. Zou, G. Cai, X. Hu, J. O. Liu, Chem Eur J 2006, 12, 7615-26.
[12] Y. Numajiri, T. Takahashi, T. Doi, Chem Asian J 2009, 4, 111-25.
[13] J. Chen, C. J. Forsyth, Org Lett 2003, 5, 1281-3.
[14] B. Zou, J. Wei, G. Cai, D. Ma, Org Lett 2003, 5, 3503-6.
[15] A. Gilles, J. Martinez, F. Cavelier, J Org Chem 2009, 74, 4298-304.
[16] H. Luesch, et al., Nat Chem Biol 2006, 2, 158-67.
[17] Y. Liu, B. K. Law, H. Luesch, Mol Pharmacol 2009, 76, 91-104.
[18] Shen, et al. J. Cell Biol 2009, 185, 629-39.
[19] R. V. Grindberg, PhD Thesis, University of California, San Diego, 2009.
[20] Gu, et al., Nature, 2009, 459, 731-5.
[21] L. Hoffmann, V. Demoulin, Belg J Bot 1991, 124, 82-8.
[22] B. N. Meyer, et al., Planta Med 1982, 45, 31-33.
[23] R. L. Manger, et al., AOAC Int 1995, 78, 521-27.
[24] B. Subramanian, et al., J Exp Ther Oncol 2006, 5, 195-204.
[25] G. L. Challis, J. Ravel, C. A. Townsend, Chemistry & Biology, 2000, 7, 211-24
[26] T. Stachelhaus, et al., Chemistry & Bilogy, 1999, 6, 493-505
[27] N. Engene, et al., J Phycol, 2010, in press.
[28] R. W. Castenholz, T. B. Norris, Algological Studies, 2005, 117, 53-69.
[29] J. Komarek, K. Anagnostidis, Cyanoprokaryota-2nd Part: Oscillatoriales in Süsswasserflora von Mitteleuropa 19/2 (Eds.: B. Büdel, L. Krienitz, G. Gärtner, M. Schagerl, Elsevier/Spektrum, Heidelberg, 2005.
[30] U. Nubel, et al., Appl Environ Microbiol, 1997, 63, 3327-32.
[31] I. Iteman, et al., Microbiology, 2000, 146, 1275-86.
[32] K. Tamura, J. Dudley, M. Nei, S. Kumar, Mol Biol Evol, 2007, 24, 1596-9.
[33] J. J. Cannone, et al., BMC Bioinformatics 2002, 3, 1471-2105.
[34] D. Posada, K. A. Crandall, Bioinformatics. 1998, 14, 817-8.
[35] S. Guindon, O. Gascuel, System. Biol. 2003, 52, 696-704, 2003.
[36] F. Ronquist, J. P. Huelsenbeck, 2003, 12, 1572-4.
[37] M. Nei, S. Kumar, Molecular Evolution and Phylogenetics, 2000, Oxford University Press, New York.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising an isolated compound consisting essentially of:
compound having the formula wherein
$R_1$=H, $CH_3$
$R_2$=H, $CH_3$, i-Pr, t-Bu
$R_3$=H, $CH_3$, i-Pr, $CH(CH_3)CH_2CH_3$, $CH_2CH(CH_3)_2$
$R_4$=H, $CH_3$, i-Pr, $CH(CH_3)CH_2CH_3$, $CH_2CH(CH_3)_2$
$R_5$=H, $CH_3$, i-Pr, $CH(CH_3)CH_2CH_3$, $CH_2CH(CH_3)_2$
$R_6$=$CH_2PhOH$, $CH_2PhOMe$, $CH_2Ph$
X=O, S, N.

2. The composition of claim 1, formulated as a pharmaceutical composition, or formulated for enteral or parenteral administration.

3. A formulation or a pharmaceutical composition comprising:
a composition of claim 1.

4. A method for decreasing or inhibiting cell growth comprising administering to a cell or contacting a cell with a composition of claim 1.

5. A method for treating and/or ameliorating:
(i) a disease or condition that can be responsive to or ameliorated by decreasing or inhibiting cell growth,
(ii) a pathological, uncontrolled or unwanted cell growth, (iii) a cancer or a metastases, or
(iv) any disease or condition or infection having a hyperproliferative cell growth component,
comprising:
(a) administering a composition of claim 1, in an amount sufficient to treat and/or ameliorate a disease or a condition:
(i) that can be treated or ameliorated by decreasing or inhibiting cell growth,
(ii) a pathological, uncontrolled or unwanted cell growth,
(iii) a cancer or a metastases, or
(iv) any disease or condition or infection having a hyperproliferative cell growth component; or
(b) the method of (a), wherein the administration is to a human or a mammal.

6. A method for ameliorating an inflammatory disease or a condition that can be ameliorated by decreasing or inhibiting cell growth or proliferation, comprising:
(a) administering a composition of claim 1, in an amount sufficient to treat or ameliorate a disease or a condition:
(i) that can be ameliorated by decreasing or inhibiting cell growth,
(ii) a pathological, uncontrolled or unwanted cell growth,
(iii) a cancer or a metastases, or
(iv) a disease or a condition or an infection having a hyperproliferative cell growth component;
(b) the method of (a), wherein the administration is to a human or a mammal.

7. A kit comprising a composition of claim 1.

8. The formulation or pharmaceutical composition of claim 3, wherein the
compound is selected from the group consisting of: an apratoxin F (compound 6 of FIG. 1); an apratoxin G (compound 7 of FIG. 1); thereof; or
(b) the formulation or pharmaceutical composition of (a), wherein the compound is formulated for administration in vivo; or for enteral or parenteral administration, or as a tablet, pill, geltab, liquid, lotion, aerosol or implant.

9. A method for decreasing or inhibiting cell growth comprising:
(a) administering to a cell or contacting a cell with a compound of claim 8; or
(b) the method of (a), wherein the administration is in vitro, ex vivo or in vivo.

10. The formulation or a pharmaceutical composition of claim 3, wherein the compound comprises an apratoxin F (compound 6 of FIG. 1).

11. The formulation or a pharmaceutical composition of claim 3, wherein the compound comprises an apratoxin G (compound 7 of FIG. 1).

12. The composition of claim 1, wherein the compound is apratoxin F (compound 6 of FIG. 1).

13. The composition of claim 1, wherein the compound is apratoxin G (compound 7 of FIG. 1).

14. The method of claim 4, wherein the administration is in vitro.

15. The method of claim 4, wherein the administration is ex vivo.

16. The method of claim 4, wherein the administration is in vivo.

17. The formulation or a pharmaceutical composition of claim 1, wherein the compound is formulated for administration in vivo.

18. The formulation or a pharmaceutical composition of claim 17, wherein the compound is formulated for enteral or parenteral administration, or as a tablet, pill, geltab, liquid, lotion, aerosol or implant.

* * * * *